United States Patent [19]

Gruis et al.

[11] Plant 4,097

[45] Sept. 6, 1977

[54] ST. AUGUSTINE GRASS

[75] Inventors: Jake T. Gruis, Apopka, Fla.; Terrance P. Riordan, Dublin; John A. Long, Marysville, both of Ohio

[73] Assignee: The O.M. Scott & Sons Company, Marysville, Ohio

[21] Appl. No.: 714,203

[22] Filed: Aug. 13, 1976

[51] Int. Cl.[2] ..... A01H 5/12

[52] U.S. Cl. ..... Plt./88

[58] Field of Search ..... Plt./88

*Primary Examiner*—Robert E. Bagwill

*Attorney, Agent, or Firm*—J. B. Raden; H. J. Holt

[57] ABSTRACT

A perennial St. Augustine grass having outstanding dark green color, rapid lateral spread, a semi-dwarf growth habit, and a medium level of flowering shoot production. This variety has good gray leafspot resistance throughout the year and is cold tolerant.

4 Drawing Figures

SUMMARY OF THE VARIETY

This invention relates to a new and distinct perennial St. Augustine grass selected from the progeny of an open pollinated purple stigma diploid parent Ea611081. This purple stigma genotype was labeled 615866 and propagated vegetatively by stolons to provide planting stock for studying performance and making comparisons to present commercial varieties.

Genotype 615866 has a wide leaf blade, a short leaf length, and an outstanding dark green color. These characteristics along with the rapid spread, its medium level of flowering shoot production, its good gray leafspot (*Piricularia grisea*) resistance, and its cold tolerance can be used to distinguish 615866 from other St. Augustine grasses.

BRIEF DESCRIPTION OF THE ILLUSTRATIONS

DETAILED DESCRIPTION OF THE VARIETY

Figure 1:
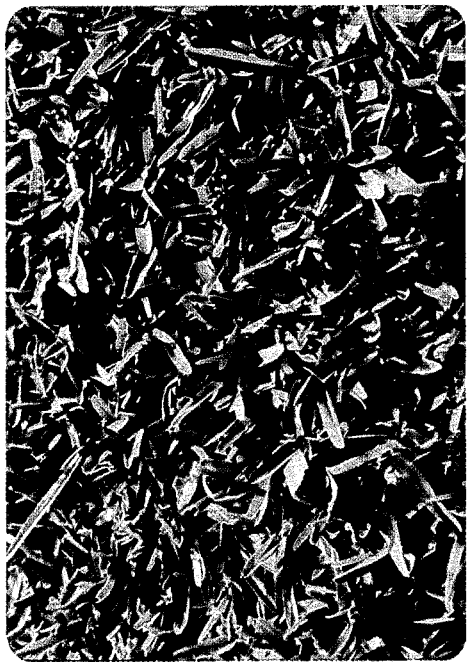
FIG. 1 is a photograph of 615866 St. Augustine turf showing generally the characteristics of this new grass.
Figure 2:
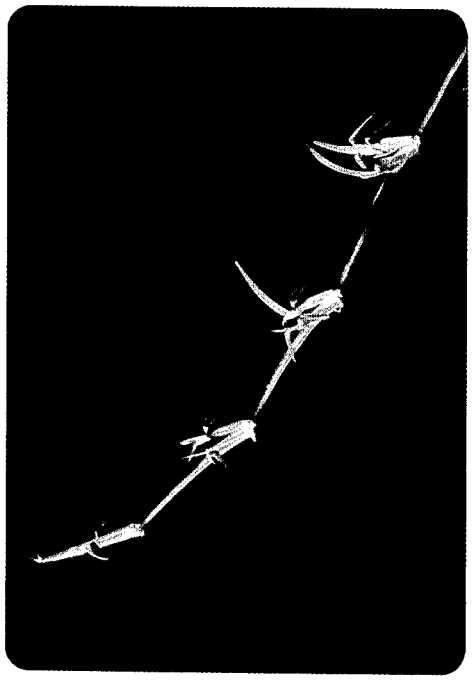
FIG. 2 shows the leaves and stem of a 615866 St. Augustine grass plant.
Figure 3:
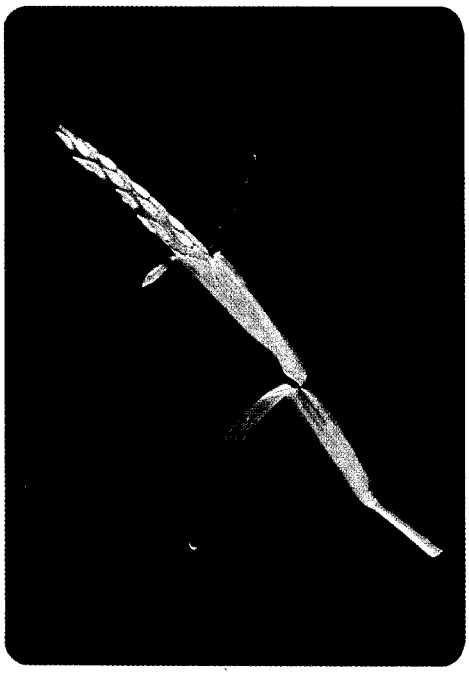
FIG. 3 shows a spike of a 615866 St. Augustine grass plant.
Figure 4:
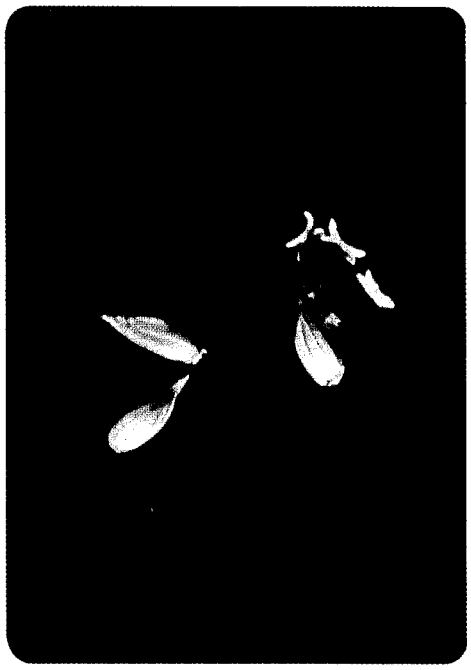
FIG. 4 shows florets of a 615866 St. Augustine grass plant.

Genotype 615866 possesses a Munsell color designation 7.5 GY 4/4 [1/] and is characterized by compressed and branched culms. The leaf blades are relatively short, averaging 44.8 mm. long, but are very coarse, averaging 7.66 mm. wide. These characteristics can be used to distinguish 615866 from both the dwarf and non-dwarf St. Augustine grasses. The average internode length is 35.0 mm., thus allowing this semi-dwarf to have a vigorous lateral spread. Genotype 615866 has a purple stigma color and an unreduced chromosome number of 18.

Total soluble salts measured in micromhos/cm. specific conductance using a Beckmann Solu-Bridge will allow differentiation between 615866 and other St. Augustine grasses. The average reading for 615866 was 146.1 micromhos/cm. The chromosome numbers, stigma colors, morphological measurements of 615866 and other St. Augustine grasses are compared in Tables 1, 2 and 3.

Table 1

Chromosome Numbers and Stigma Colors of 615866 and other St. Augustine grasses

| Selection/Variety | Chromosome Number (Unreduced)[2] | Stigma Color |
|---|---|---|
| 615866 | 18 | Purple |
| 45176 | 18 | " |
| 73176 | 18 | " |
| Ea611081 | 18 | " |
| Floratine | 27 | " |
| Bitter Blue | 27 | " |
| Texas Common | 18 | White |

[1]The Munsell designated color is of plant material grown in the greenhouse. The color is subject to variation depending upon the environmental conditions under which the grass is grown.

[2]Chromosome Number determinations made on pollen mother cells.

Table 2

Comparative Leaf Blade Length, Width and Internode Length for 615866 and Other St. Augustine grasses

| Selection/ Variety | Leaf Blade Length (mm.)[1] | Leaf Blade Width (mm.)[2] | Internode Length (mm.)[3] |
|---|---|---|---|
| 615866 | 44.8 ± 11.6 | 7.66 ± 0.72 | 35.0 ± 7.7 |
| 45176 | 44.2 ± 11.8 | 6.04 ± 0.89 | 22.8 ± 3.8 |
| 73176 | 33.4 ± 7.3 | 5.86 ± 1.09 | 10.8 ± 2.2 |
| Ea611081 | 78.4 ± 33.3 | 7.12 ± 1.38 | 36.0 ± 7.4 |
| Floratine | 82.8 ± 25.9 | 7.81 ± 2.46 | 36.3 ± 7.3 |
| Bitter Blue | 105.2 ± 31.8 | 8.55 ± 1.25 | 38.3 ± 8.7 |
| Texas Common | 45.0 ± 16.8 | 6.48 ± 0.85 | 34.0 ± 4.2 |
| LSD 5% | 12.1 | .71 | 4.0 |

[1]All plant material grown unclipped in greenhouse.

[2]Measurements recorded 15 millimeters above leaf collar.

[3]Measurements recorded between third and fourth internodes.

Table 3

Specific Conductance Measurements of 615866 and Other St. Augustine grasses

| Selection/Variety | Specific Conductance (micromhos/cm.)[1] |
|---|---|
| 615866 | 146.1 |
| 45176 | 104.1 |
| 73176 | 107.3 |
| Ea611081 | 132.3 |
| Bitter Blue | 190.2 |
| Texas Common | 122.8 |

[1]Measurements were made on a six centimeter stem section.

The characteristic growth habit can be used to distinguish 615866 from the dwarf St. Augustine grasses 73176 and 45176, and the more upright growing types Bitter Blue and Texas Common. In addition, fresh weight clipping yields can be used to distinguish 615866 from the two dwarf selections and Ea611081. This information is illustrated in Tables 4 and 5. In Table 6 it can be seen that the leaf texture of 615866 is similar to that of the coarser types Bitter Blue and Texas Common thus differentiation in these cases must be based on the lower growth habit of 615866.

Table 4

Comparative Growth Habit Averages for 615866 and Other St. Augustine grasses at Apopka, Florida, and Katy, Texas

| Selection/ Variety | Growth Habit[1] Florida 1971 | Texas 1971 | Florida 1972 |
|---|---|---|---|
| 615886 | 3.4 | 4.1 | 3.0 |
| 45176 | 2.6 | 2.5 | 2.1 |
| 73176 | 2.4 | 2.5 | 1.6 |
| Ea611081 | 3.4 | 4.0 | 3.2 |
| Bitter Blue | 4.4 | 4.5 | 3.7 |
| Texas Common | — | — | — |
| | — | — | .2 |

[1]Rating 1 - low growing, 5- upright growing

Table 5

Fresh weights of Clippings Removed From Plots of 615866 and Other St. Augustine grasses

| Selection/ Variety | Fresh Weights (gms/.48m × 1.52 m plot) July | August | September |
|---|---|---|---|
| 615866 | 24.7 ± 9.1 | 40.0 ± 15.1 | 38.3 ± 8.7 |
| 45176 | 6.3 ± 2.1 | 19.7 ± 10.0 | 13.7 ± 6.4 |
| 73176 | 3.0 ± 1.7 | 6.0 ± 3.6 | 7.7 ± 2.9 |
| Ea611081 | 36.7 ± 12.9 | 74.0 ± 12.5 | 45.0 ± 8.2 |
| Bitter Blue | 22.3 ± 9.9 | 43.7 ± 15.3 | 29.7 ± 4.9 |
| LSD 5% | 16.6 | 21.8 | 11.0 |

Table 6

Comparative Texture Averages for 615866 and Other St. Augustine grasses at Apopka, Florida, and Katy, Texas

| Selection/ Variety | Texture[1] Florida 1971 | Texas 1971 | Florida 1972 |
|---|---|---|---|
| 615866 | 1.9 | 1.7 | 2.3 |
| 45176 | 2.7 | 2.1 | 3.0 |
| 73176 | 2.9 | 2.5 | 3.1 |
| Ea611081 | 1.7 | 2.0 | 2.3 |
| Bitter Blue | 1.4 | 1.5 | 2.0 |
| Texas Common | — | 1.1 | — |
| LSD 5% | — | — | .2 |

Genotype 615866 has an outstanding dark green color and a medium level of flowering shoot production. Field observations have shown that 615866 has the fastest rate of cover of any St. Augustine grass tested including Ea611081. The observations of color and rate of cover used in combination can allow distinction of 615866 from Ea611081. This information is illustrated in Tables 7, 8 and 9.

Table 7

Comparative Color Averages for 615866 and Other St. Augustine grasses at Apopka, Florida, and Katy, Texas

| Selection/ Variety | Color[1] Florida 1971 | Texas 1971 | Florida 1972 |
|---|---|---|---|
| 615866 | 9.4 | 8.9 | 8.0 |
| 45176 | 8.7 | 9.3 | 7.9 |
| 73176 | 8.9 | 9.3 | 8.1 |
| Ea611081 | 8.7 | 8.7 | 7.8 |
| Bitter Blue | 9.1 | 8.7 | 7.8 |
| Texas Common | — | 8.8 | — |
| LSD 5% | — | — | .2 |

[1]Rating 1 - lightest green, 10 - darkest green

Table 8

Comparative Ratings of Average Flowering Shoot Production of 615866 and Other St. Augustine grasses at Apopka, Florida, and Katy, Texas

| Selection Variety | Average Flowering Shoot Production[1] Texas 9/17/71 | Florida 6/15/72 |
|---|---|---|
| 615966 | 1 | 2.3 |
| 45176 | 3 | 2.3 |
| 73176 | 0 | .7 |
| Ea611081 | 0 | 2.0 |
| Bitter Blue | 0 | 1.3 |
| Texas Common | 3 | — |
| LSD 10% | — | 1.0 |

[1]Rating 0 - no flowering shoot production, 5 - heavy flowering shoot production.

Table 9

Relative Comparison of Percent Turf Cover of 615866 and Other St. Augustine grasses at Apcpka, Florida

| Selection/ Variety | Average Percent Area Covered[1] 2/15/72 | 4/3/72 | | 5/1/72 |
|---|---|---|---|---|
| 615866 | 53 | 60 | 97 | 100 |
| 45176 | 37 | 47 | 60 | 93 |
| 73176 | 40 | 47 | 67 | 93 |
| Ea611081 | 57 | 60 | 87 | 97 |
| Bitter Blue | 47 | 53 | 70 | 97 |
| LSD 5% | 8 | 10 | 15 | N.S. |

[1]Initial planting made 12/1/71

Genotype 615866 has a lower percent gray leafspot (*Piricularia grisea*) infestation throughout the whole year than any selection other than the very leafspot resistant dwarf 73176. This observation can be used to distinguish 615866 from other less resistant selections such as Bitter Blue and Texas Common. This information is given in Table 10.

Table 10

Comparative Gray Leafspot (*Piricularia Grisea*) Resistance of 7615866 and Other St. Augustine grasses at Apopka, Florida and Katy, Texas.

| Selection/ Variety | Percent Gray Leafspot Florida 6/28/71 | Texas 4/31/71 | 6/29/71 | 7/31/71 | 9/2/71 | 9/17/71 |
|---|---|---|---|---|---|---|
| 615866 | 20 | 10 | 10 | 10 | 10 | 0 |
| 45176 | 20 | 20 | 30 | 10 | 20 | 30 |
| 73176 | 20 | 10 | 20 | 10 | 5 | 0 |
| Ea611081 | 20 | 10 | 30 | 20 | 10 | 30 |
| Bitter Blue | 40 | 90 | 10 | 10 | 10 | 20 |
| Texas Common | — | 10 | 60 | 20 | 30 | 20 |

The cold tolerance of 615866 and other St. Augustine grasses is shown in Table 11. The cold tolerance of this genotype allows differentiation from other less tolerant St. Augustine grasses under sub-zero (centigrade) stress.

Table 11

Comparative Cold Damage from Below Zero (centigrade) Temperature of 615866 and Other St. Augustine grasses in Apopka, Florida and Katy, Texas

| Selection/ Variety | Percent Cold Damage[1] Texas 1972 | Florida 1973 Test - A[2] | Florida 1973 Test - B[3] |
|---|---|---|---|
| 615866 | 0 | 5 | 27.5 |
| 45176 | 95 | 60 | 47.5 |
| 73176 | 99 | 40 | 35.0 |
| Ea611081 | 99 | 15 | 50.0 |

Table 11-continued

Comparative Cold Damage from Below Zero (centigrade) Temperature of 615866 and Other St. Augustine grasses in Apopka, Florida and Katy, Texas

| Selection/ Variety | Percent Cold Damage[1] Texas 1972 | Florida 1973 Test - A[2] | Florida 1973 Test - B[3] |
|---|---|---|---|
| Bitter Blue | 20 | 5 | 52.5 |
| Texas Common | 0 | — | — |

[1]Cold damage as measured by percent stolons killed.
[2]Test - A, Two year old sod.
[3]Test - B, One year old sod.

What is claimed and desired to be secured by Letters Patent is:

1. A St. Augustine grass, substantially as herein illustrated and described.

* * * * *